United States Patent
Kohl et al.

(10) Patent No.: US 6,961,600 B2
(45) Date of Patent: Nov. 1, 2005

(54) TRANSBRONCHIAL REFLECTANCE OXIMETRIC MEASUREMENT OF MIXED VENOUS OXYGEN SATURATION, AND DEVICE THEREFOR

(75) Inventors: Benjamin A. Kohl, Philadelphia, PA (US); Noah A. Rosen, Jamaica Plain, MA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 143 days.

(21) Appl. No.: 10/365,178

(22) Filed: Feb. 12, 2003

(65) Prior Publication Data

US 2003/0181797 A1 Sep. 25, 2003

Related U.S. Application Data

(60) Provisional application No. 60/356,668, filed on Feb. 13, 2002.

(51) Int. Cl.[7] .................................................. A61B 5/00
(52) U.S. Cl. ...................................... 600/339; 600/341
(58) Field of Search .................................. 600/310, 322, 600/323, 339, 341

(56) References Cited

U.S. PATENT DOCUMENTS

| | | | | |
|---|---|---|---|---|
| 3,847,483 A | * | 11/1974 | Shaw et al. ................... | 356/41 |
| 5,005,573 A | * | 4/1991 | Buchanan ..................... | 600/338 |
| 5,111,817 A | * | 5/1992 | Clark et al. .................. | 600/323 |
| 5,127,408 A | * | 7/1992 | Parsons et al. ............... | 600/342 |
| 5,329,922 A | * | 7/1994 | Atlee, III ..................... | 600/342 |
| 5,357,954 A | * | 10/1994 | Shigezawa et al. ........... | 600/339 |
| 5,417,207 A | * | 5/1995 | Young et al. ................. | 600/323 |
| 5,715,816 A | * | 2/1998 | Mainiero et al. ............. | 600/323 |
| 5,954,050 A | * | 9/1999 | Christopher ............. | 128/204.23 |
| 6,071,237 A | * | 6/2000 | Weil et al. ................... | 600/342 |
| 6,073,037 A | | 6/2000 | Alam et al. | |

OTHER PUBLICATIONS

Baele, P.L., McMichan, J.C., Marsh, H.M., Sill, J.C., and Southorn, P.A., "Continuous monitoring of mixed venous oxygen saturation in critically ill patients," *Anesth. Analg.* 61:513 (1982).

Baldwin, I.C., and Heland, M., "Incidence of cardiac dysrhythmias in patients during pulmonary artery catheter removal after cardiac surgery," *Heart Lung* 29:155 (2000).

Boscoe, M.J. and de Lange, S., "Damage to the tricuspid valve with a Swan–Ganz catheter," *BMJ* 283:346 (1981).

(Continued)

*Primary Examiner*—Eric F. Winakur
(74) *Attorney, Agent, or Firm*—Evelyn H. McConalty; Drinker Biddle & Reath (57) ABSTRACT

Provided are methods and a system for the transbronchial reflectance oximetric measurement of mixed venous oxygen saturation in the pulmonary artery of a patient, and a device therefor. Thus, provided is a quick, minimally invasive, method and system for determining an important endpoint of resuscitation, particularly for a patient in shock, because the probe used to measure the venous oxygen saturation is configured to permit insertion through an endotracheal tube until the probe is placed in contact with the bronchial luminus mucosa of the patient's right bronchus, left bronchus or distal trachea, directly adjacent to the patient's pulmonary artery.

24 Claims, 3 Drawing Sheets

OTHER PUBLICATIONS

Boyd, K.D., Thomas, S.J., and Gold, J., "A prospective study of complications of pulmonary artery catheterizations in 500 consecutive patients," *Chest* 84:245 (1983).

Brimacombe, J., Keller, C., and Margreiter, J., "A pilot study of left tracheal pulse oximetry," *Anesth. Analg.* 91:1003 (2000).

De Lima, L.G., Wynands, J.E., Bourke, M.E., and Walley, V.M., "Catheter–induced pulmonary artery false aneurysm and rupture: case report and review," *J. Cardiothoracic Vasc. Anesth.* 8:70 (1994).

Ducatman, B.S., McMichan, J.C., and Edwards, J.E., "Local complications associated with indwelling Swan–Ganz catheters: A one–year prospective study of 141 autopsies," *JAMA* 253:791 (1985).

Edwards, J.D., and Mayall, R.M., "Importance of the sampling site for measurement of mixed venous oxygen saturation in shock," *Crit. Care Med.* 26:1356 (1998).

Elliott, C.G., Zimmerman, G.A., and Clemmer, T.P., "Complications of pulmonary artery catheterization in the care of critically ill patients. A prospective study," *Chest* 76:647 (1979).

Foote, G.A., Schabel, S.I., and Hodges, M.H., "Pulmonary complications of the flow directed balloon–tipped catheter," *N. Engl. J. Med.* 290:927 (1974).

Fowler, N.O., Westcott, R.N., and Scott, R.C., "Disturbances in cardiac mechanism of several hours duration complicating cardiac venous catheterization," *Am. Heart J.* 46:652 (1951).

Gattinoni, L, Brazzi, L., Pelosi, P., Latini, R., Tognoni, G., Pesenti, A., and Fumagalli, R., "A trial of goal–directed hemodynamic therapy in critically ill patients," *N. Engl. J. Med.* 333;1025 (1995).

Greenall, M.J., Blewett, R.W., and McMahon, M.J., "Cardiac tamponade and central venous catheters," *BMJ* 2:595 (1975).

Henzel, J.W., and DeWeese, M.S., "Morbid and mortal complications associated with prolonged central venous cannulation: awareness, recognition, and prevention,"*Am. J. Surg.* 121:600 (1971).

Hull, E.L., and Foster, T.H., "Noninvasive Near–Infrared Hemoglobin Spectroscopy for in–vivo Monitoring of Tumor Oxygenation and Response to Oxygen Modifiers," In *Optical Tomography and Spectroscopy of Tissue: Theory, Instrumentation, Model and Human Studies II*, Chance, B., and Alfano, R.R. (eds.), *SPIE Proc.* 2979:355 (1997).

Katz, J.D., Cronau, L.H., and Barash, P.G., "Pulmonary artery flow–guided catheters in the perioperative period. Indications and Complications," *JAMA* 237:2832 (1977).

Margreiter, J., Keller, C., and Brimacombe, J., "The Feasibility of Transesophogeal Echocardiograph–Guided Right and Left Ventricular Oximetry in Hemodynamically Stable Patients Undergoing Coronary Artery Bypass Grafting," *Anesth. Analg.* 94:794 (2002).

McDaniel, D.D., Stone, J.G., and Faltas, A.N., "Catheterinduced pulmonary artery hemorrhage. Diagnosis and management in cardiac operations," *J. Thorac. Cardiovasc. Surg.* 82:1 (1981).

Mermel, L.A., McCormick, R.D., and Springman, S.R., "The pathogenesis and epidemology of catheter–related infection with pulmonary artery Swan–Ganz catheters: a prospective study utilizing molecular subtyping," *Am. J. Med.* 91:197S (1991).

Michel, L., Marsh, H.M., and McMichan, J.C., "Infection of pulmonary artery catheters in critically ill patients," *JAMA* 245:1032 (1981).

Morris, D., Mulvihill, D., and Lew, W.Y., "Risk of developing complete heart block during bedside pulmonary artery catheterization in patients with left bundle–branch block," *Arch. Intern Med.* 147:2005 (1987).

O'Toole, J.D., Wurtzbacher, J.J., Wearner, N.E., and Jain, A.C., "Pulmonary–valve injury and insufficiency during pulmonary–artery catheterization," *NEJM* 301:1167 (1979).

Patil, A.R., "Risk of right bundle–branch block and complete heart block during pulmonary artery catheterization [letter]," *Crit. Care Med.* 18:122 (1990).

Puri, V.K., Carlson, R.W., Bander, J.J., and Weil M.H., "Complications of vascular catheterization in the critically ill," *Crit. Care Med.* 8: 495 (1980).

Risk, S.C., Brandon, D., and D'Ambra, M.N., "Indications for the use of pacing pulmonary artery catheters in cardiac surgery," *J. Cardiothoracic Vasc. Anesth.* 2:275, 1992.

Rivers, E., Nguyen, B., Havstad, S., Ressler, J., Muzzin, A., Knoblich, B., Petersen, E., and Tomlanovich, M., "Early goal–directed therapy in the treatment of severe sepsis and septic shock," *N. Engl. J. Med.* 345:1368 (2001).

Robin, E.D., "Death by pulmonary artery flow–directed catheter. Time for a moratorium?," *Chest* 92:727 (1987).

Schwartz, K.V., and Garcia, F.G., "Entanglement of Swan–Ganz catheter around an intracardiac structure," *JAMA* 237:113 (1987).

Shah, K.B., Rao, T.L.K., and Laughlin, S., "A review of pulmonary artery catheterization in 6,245 patients," *Anesthesiology* 61:271 (1984).

Sise, M.J., Hollingsworth P., and Brimm J., "Complications of the flow–directed pulmonary–artery catheter: a prospective analysis of 219 patients," *Crit. Care Med.* 9:315 (1981).

Sprung, C.L., Elser, B., and Schein, M.H., "Risk of right bundle–branch block and complete heart block during pulmonary artery catheterization," *Crit. Care Med.* 17:1 (1989).

Svedjeholm, R., Hakanson, E., and Szabo, Z., "Routine SVO2 measurement after CABG surgery with a surgically introduced pulmonary artery catheter," *Eur. J. of Cardio-Thor. Surg.* 16:450 (1999).

Takatani, S., and Ling, J., "Optical oximetry sensors for whole blood and tissue," *IEEE Eng. Med. Biol. Mag.* 3:347 (1994).

Zilstra, W.G., Buursma, A. and van Assendelft, O.W., In *Visible and Near Infrared Absorption Spectra of Human and Animal Haemoglobin*, Utrecht: VSP, pp. 262 (2000).

Zonios, G., Perelman, L.T., Backman, V., and Manoharan, R., "Diffuse Reflectance Spectroscopy of Human Adenomatous Colon Polyps in vivo," *Applied Optics* 38(31):6628 (1999).

\* cited by examiner

TRANSBRONCHIAL REFLECTANCE OXIMETRIC MEASUREMENT OF MIXED VENOUS OXYGEN SATURATION, AND DEVICE THEREFOR

REFERENCE TO RELATED APPLICATION

This application claims priority to U.S. Provisional Application No. 60/356,668, filed Feb. 13, 2002, the content of which is herein incorporated by reference.

FIELD OF THE INVENTION

The present invention is in the field of transbronchial oximetric measurement, and discloses the feasibility and accuracy of measuring mixed venous oxygen saturation within the pulmonary artery.

BACKGROUND OF THE INVENTION

Shock is a state of global tissue hypoxia. Pulse oximetry is widely used in anesthesia and critical care medicine to provide noninvasive information about arterial oxygen saturation ($SaO_2$). The oximeter uses either the transmission or reflectance of near-infrared light to monitor the changes in the hemoglobin spectrum with oxygenation and deoxygenation. Oximetry probes are usually applied to a patient's fingers or ears for convenience, but this has a signal acquisition failure rate of 1.12% to 2.5% (Reich et al., *Anesthesiology* 84:859–864 (1996); Severinghaus et al., *Anesthesiology* 76:1018–1038 (1992); Moller et al., *Anesthesiology* 78:445–453 (1993)), and more accurate readings can be obtained from better-perfused superficial tissues, such as the cheek (O'Leary et al., *Anesth. Analg.* 75:495–498 (1992)), nasal septum (Ezri et al., *J. Clin. Anesth.* 3:447–450 (1991)), and tongue (Jobes et al., *Anesth. Analg.* 67:186–188 (1988)). More recently, oximeters have been placed into deep, vessel-rich areas, such as the esophagus (Vicenzi et al., *Crit. Care Med.* 28:2268–2270 (2000)), pharynx (Keller et al., *Anesth. Analg.* 90:440–444 (2000); Brimacombe et al., *Can. J. Anaesth.* 47:907–909 (2000)), and trachea (Brimacombe et al., *Anesth Analg.* 91:1003–1006 (2000)) where, because the heart lies in close proximity to the esophagus, esophageal oximetry readings seem to provide more accurate readings than surface oximetry, even in hypoperfusion states. Appropriately located and directed esophageal oximetry probe have been used to derive oximetry readings from specific ventricular locations within the heart (Margreiter et al., *Anesth. Analg.* 94:794–798 (2002)). The resulting transesophageal echocardiography (TEE) permits the measurement of cardiac performance during surgery, but it involves passing an endoscope into the esophagus of the patient and the use of ultrasound imaging technology (Bryan et al., *Ann. Thorac. Surg.* 59:773–779 (1995)).

The mixed venous oxygen saturation ($SVO_2$) of blood in the pulmonary artery has emerged as an important monitor of the balance between oxygen delivery and oxygen demand. In a prospective randomized study of critically ill patients, a direct comparison of a resuscitation strategy based on the normalization of cardiac index and one based on the normalization of mixed venous saturation were reported to have equivalent efficacy in predicting a clinical course of treatment (Gattinoni et al., *N. Engl. J. Med.* 333:1025 (1995)). Several studies have shown that mixed venous oxygen saturation has significant prognostic value in the perioperative period (e.g., Svedjeholm et al., *Eur. J. of Cardio-Thor. Surg.* 16:450 (1999)).

The determination of mixed venous saturation requires the measurement of the oxygen saturation of blood from the pulmonary artery. This can be accomplished using a fiber-optic oximeter coupled to a pulmonary artery catheter (Baele et al., *Anesth. Analg.* 61:513 (1982)). The oximeter uses the reflectance of near-infrared light to monitor the changes in the hemoglobin spectrum with oxygenation and deoxygenation. One commercially available fiber optic oximeter (Abbott Laboratories, Abbott Park, Ill.) measures the reflectance of three wavelengths of light (670, 700, 800 nm) and applies an empirically derived polynomial function to calculate saturation (Zilstra et al., In *Visible and Near Infrared Absorption Spectra of Human and Animal Haemoglobin*, Utrecht: VSP, pp. 262 (2000)).

Nevertheless, there are no techniques currently available for continuous noninvasive measurement of the oxygen saturation of blood flowing through the heart. Placement of a pulmonary artery catheter is an invasive procedure with many possible complications. These include bleeding, infection, pneumothorax, arrhythmia, and pulmonary artery rupture (see Table 1). Puri et al., (*Crit. Care Med.* 8: 495, (1980)) found at least a 10% incidence of complications with the placement of pulmonary artery catheters by critical care fellows.

TABLE 1

| Common Complications | Incidence | Reference |
| --- | --- | --- |
| Minor transient arrhythmias | 4.7%–69% | Sise et al., Crit. Care Med. 9:315 (1981); |
| Transient VT or VF | 0.3%–63% | Katz et al., JAMA 237:2832 (1977); Boyd et |
| Overall risk of transient arrhythmia | 48% | al., Chest 84:245 (1983). |
| Right Bundle Branch Block | 0.1%–4.3% | Fowler et al., Am. Heart J. 46:652 (1951); Shah et al., Anesthesiology 61:271 (1984); Morris et al., Arch. Intern Med. 147:2005 (1987); Patil, Crit. Care Med. 18:122 (1990); Sprung et al., Crit. Care Med. 17:1 (1989) |
| Complete heart block (in patients with pre-existing LBBB) | <1% | Shah et al., 1984; De Lima et al., J. Cardiothoracic Vasc. Anesth. 8:70 (1994) |
| VT (with hypotension) associated with removal of PAC | 2% | Baldwin et al., Heart Lung 29:155 (2000). |
| Infection at insertion site | 0%–22% | Michel et al., JAMA 245:1032 (1981); Mermel et al., Am. J. Med. 91:197S (1991). |
| Catheter related sepsis[a] | 0%–2% | Shah et al., 1984; Patil, 19903 |
| Mural thrombus[b] | 28%–61% | Patil, 1990; Sprung et al., 1989 |

TABLE 1-continued

| | | |
|---|---|---|
| Pulmonary infarction | 0.1%–7% | Boyd et al., 1983; Foote, et al., N. Engl. J Med. 290:927 (1974); Elliott et al., Chest 76:647 (1979). |
| Uncommon Complications | | |
| Pulmonary artery false aneurysm | 0.06%–0.2% | De Lima et al., 1994; Robin, Chest 92:727 (1987). |
| Pulmonary artery rupture | <1% | Shah et al., 1984; McDaniel et al., J Thorac. Cardiovasc. Surg. 82:1 (1981) |
| Pneumothorax | <1% | Sise et al., 1981; Shah et al., 1984 |
| Cardiac tamponade due to catheter induced perforation | <1% | Sise et al., 1981; Shah et al., 1984, Elliott et al., 1979; Greenall et al., BMJ 2:595 (1975) |
| Catheter knotting | <1% | Schwartz et al., JAMA 237:113 (1987) |
| Valvular damage | <1% | Boscoe et al., BMJ 283:346 (1981); O'Toole et al., NEJM 301:1167 (1979). |

[a]Risk increases significantly when catheter is in place >3–4 days.
[b]Significance unknown Due to the high potential for complication, the placement of pulmonary artery catheters is often delayed or foregone altogether. A recent prospective randomized trial studied the use of early goal-directed therapy in patients with septic shock begun in the emergency room, and found a decrease in hospital mortality from 46.5% to 30.5% (Rivers et al., N. Engl. J. Med. 345:1368 (2001)). However, in that study, they could not measure mixed venous saturation, as the insertion of pulmonary artery catheters was impractical. Instead the investigators used the poor surrogate of central venous saturation as a guide for resuscitation (Edwards et al., Crit Care Med. 26:1356 (1998)). Perhaps early intervention would have proven to be even more beneficial if mixed venous saturation could have quickly and easily been measured.

SUMMARY OF THE INVENTION

The present invention provides a novel approach for measuring in vivo the mixed venous oxygen saturation within the pulmonary artery of a patient. A near-infrared reflectance spectroscopy source/detector is placed within the distal trachea, left mainstem bronchus or right mainstem bronchus of a patient, directly adjacent to the patient's pulmonary artery, preferably in a human patient. Most often the patient is already intubated or an endotracheal tube is being inserted as a routine part of the course of treatment for that patient. Thus, the process itself is noninvasive to the patient since an endotracheal tube is already in place—i.e., in an emergency room situation or during surgery or in a patient in shock, wherein the process is of greatest value in a resuscitation strategy. To demonstrate the value of this approach, the mixed venous oxygen saturation measurement as determined by the present invention is compared with the values established by a pulmonary artery catheter within the pulmonary artery of the same patent or animal subject.

Accordingly the transbronchial measurement of mixed venous oxygen saturation, in accordance with the methods, system and device of the present invention, provides a quick, minimally invasive, method to determine an important endpoint of resuscitation in a patient.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended figures.

DESCRIPTION OF PREFERRED EMBODIMENTS OF THE INVENTION

In patient resuscitation strategies, early goal-directed therapy has been shown to improve mortality. Transbronchial measurement of mixed venous oxygen saturation, in accordance with the methods, system and device of the present invention, provides a quick, minimally invasive, method to determine an important endpoint of resuscitation, particularly for a patient in shock. Determination of mixed venous oxygen saturation requires measurement of the oxygen saturation of blood from the pulmonary artery. Mixed venous oxygen saturation ($SVO_2$), measured in the pulmonary artery, is an important indicator of shock and resuscitation.

Currently the measurement of $SVO_2$ requires placement of a pulmonary artery catheter, which is a time-consuming invasive procedure with many possible complications. However, in an intubated patient in shock, a bronchoscope can be used with minimal difficulty or risk to the patient. In a preferred embodiment of the present invention, a fiber-optic probe is inserted through an endotracheal tube, and advanced until it is in contact with the mucosa of the right bronchus, left bronchus or distal trachea directly adjacent to the pulmonary artery.

Anatomically, the left pulmonary artery lies adjacent to the left mainstem bronchus (either mainstem or intermedius). A review of twenty, randomly-selected thoracic computed tomographic images revealed the following measurements:

| | |
|---|---|
| Thickness of bronchial wall | 0.4–1.5 mm |
| Diameter of bronchus | 10–13 mm |
| Distance from bronchial mucosa to pulmonary artery lumen | 1–2 mm |
| Diameter of pulmonary artery | 13–18 mm |

Near infrared light can penetrate deep into tissue (1–10 mm) (U.S. Pat. No. 6,073,037, Alam et al., issued 2000), meaning that these measurements are well within its range of penetration.

Most patients in shock are intubated, thereby providing easy access to the trachea and bronchi. Thus, it is feasible, without additional discomfort or trauma to the patient, to provide a continuous or rapid measurement of mixed venous oxygen saturation in the pulmonary artery using a reflectance fiber-optic probe placed in the left mainstem bronchus, right mainstem bronchus or distal trachea. Such early goal-directed therapy provides a means to improve mortality of a patient, particularly one in shock. Moreover, by repeating the quantitative measurements made via the fiber-optic probe, a pattern is created indicating a change in oxygen consumption, a change in hemoglobin concentration, and/or a change in cardiac output in the patient.

The present invention is further described by example. The embodied methods, system and device are applicable to any mammalian subject, although human subjects are preferred. Accepted animal models are used the test the methods and device of the present invention, and the findings are then applicable to all mammalian species, including humans, wherein the right bronchus, left bronchus or distal trachea is directly adjacent to the pulmonary artery (see FIG. 3). Nevertheless, the following examples are not to be construed as limiting the scope of the appended claims.

EXAMPLES

Example 1

Determining Pulmonary Artery Saturation Using Reflectance Near-Infrared Spectroscopy in an Ex-Vivo En-Bloc Preparation.

Figure 1:
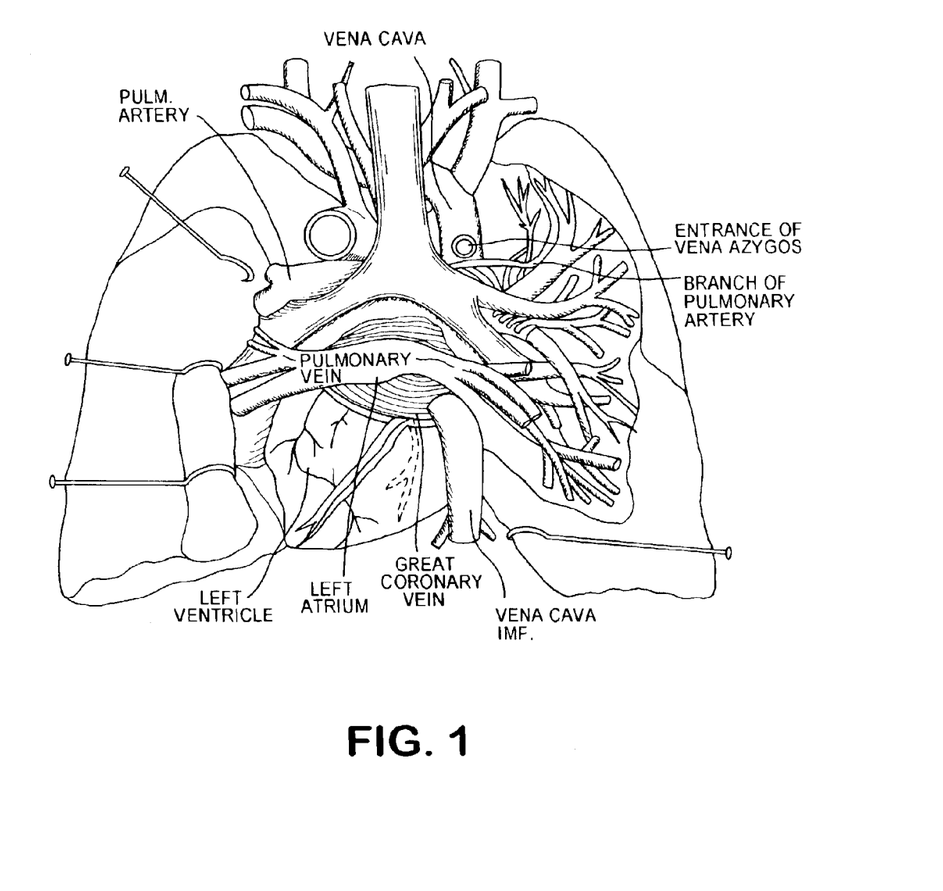
FIG. 1 shows an illustration of a coronal section of the human thoracic cavity. Various regions of the bronchus (right mainstem, left mainstem and distal trachea) abut regions of pulmonary artery.
Figure 2:
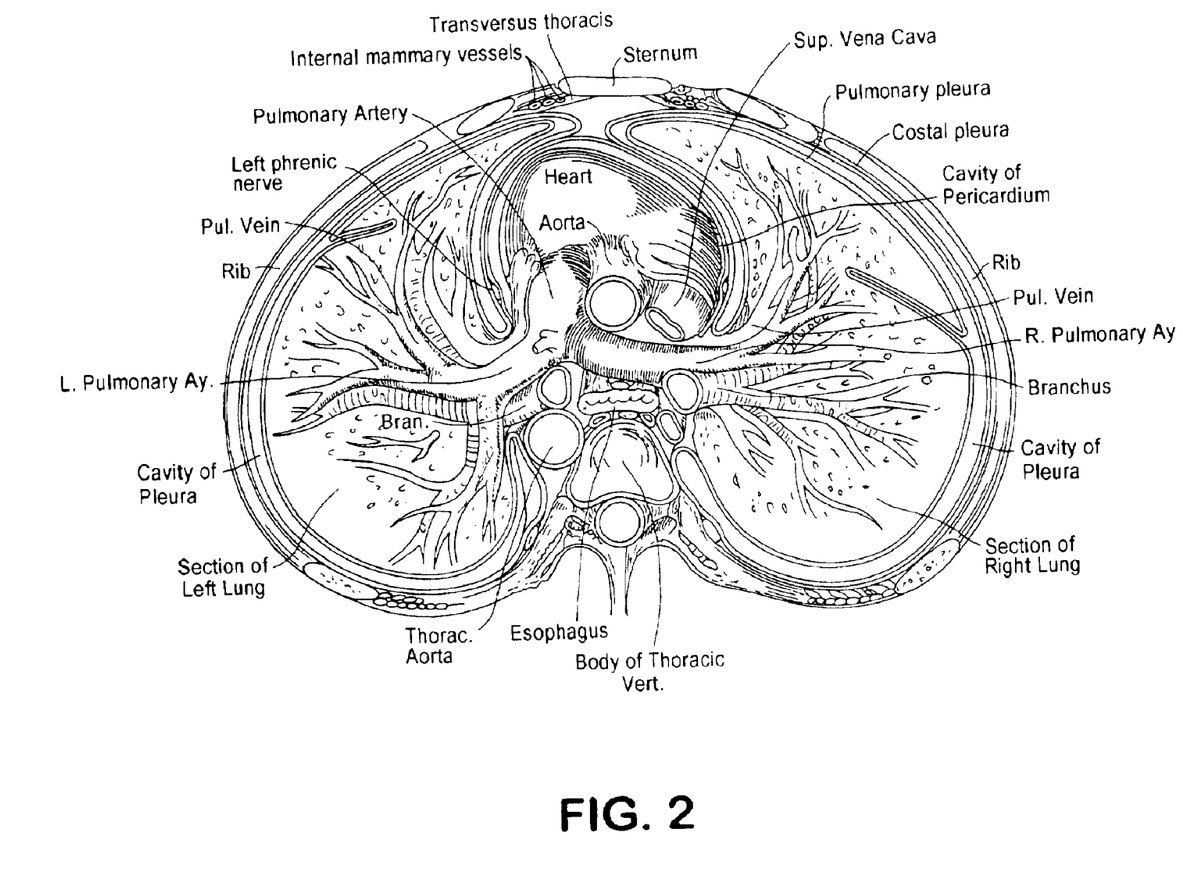
FIG. 2 illustrates an axial section of human thorax at the level of the right and left pulmonary artery bifurcation.

Fresh cadaveric samples of the right pulmonary artery, anatomically associated with the right bronchus, from sheep are obtained. A fiber-optic probe is inserted into the right bronchus through an incision on the wall opposite the pulmonary artery, and advanced until it is in contact with the mucosa of the bronchus directly adjacent to the pulmonary artery (FIG. 1 and FIG. 2). Heparinized blood (e.g., sheep blood) is circulated through the pulmonary artery segment via a pump at varying flow rates, while temperature is held constant at 37° C.

The saturation of the blood is changed by bubbling varying concentrations of humidified oxygen and nitrogen gas through it. The effect of hemoglobin concentration ([Hb]) is determined by dilution of the blood with saline. When the blood is sampled, the reference values of saturation and [Hb] are determined using a co-oximeter. The fiber optic probe records reflectance spectra from 600–1000 nm. The spectra are analyzed to determine an empiric relationship between the reflectance at two or more wavelengths that can be used to estimate oxygen saturation independent of [Hb] and flow effects.

Example 2

Determining Pulmonary Artery Saturation Using Reflectance Near-Infrared Spectroscopy In-Vivo.

The thorax of a sheep is entered via median sternotomy. The right bronchus and adjacent pulmonary artery are dissected. As in the ex-vivo experiment in Example 1, a fiber-optic probe is inserted into the right bronchus through an incision on the wall opposite the pulmonary artery, and advanced until it is in contact with the mucosa of the bronchus directly adjacent to the pulmonary artery (see FIG. 3). The opening in the bronchus is closed with a purse string suture and ventilation of both lungs is continued. A pulmonary artery catheter is placed and blood is sampled for reference measurements of saturation and [Hb] using a co-oximeter. Hemoglobin concentration is varied in vivo by exsanguination, while arterial oxygen saturation is changed by varying the concentration of oxygen in the fresh, incoming gas flow mixture.

By rearranging the Fick equation as follows, one can see that if the arterial oxygen saturation, oxygen consumption, and hemoglobin concentration are held relatively constant, mixed venous oxygen concentration varies directly with cardiac output.

$$SVO_2 = SaO_2 - VO_2/(13.4 \times CO \times [Hb]) \quad \text{(Equation 1)}$$

wherein $SVO_2$=mixed venous oxygen saturation; $SaO_2$=arterial oxygen saturation; $VO_2$=oxygen consumption; CO=cardiac output [L/min]; Hb=hemoglobin concentration [g/dL].

The fiber optic probe, therefore, measures the scatter of light reflected by oxygenated hemoglobin, from which deoxygenated hemoglobin is subtracted, thereby quantitatively determining mixed venous oxygen saturation in the pulmonary artery of the patient. The probe records reflectance spectra from 600–1000 nm. The spectra are analyzed to determine an empiric relationship between the reflectance at two or more wavelengths that can also be used to estimate oxygen saturation independent of [Hb]. These results are then compared with those from the ex-vivo experiment. Thus, the value produced during diastolic phase of blood flow provides a quantitative measurement of venous oxygen saturation during pulsatile blood flow in the pulmonary artery.

In a preferred embodiment of the invention, the algorithm set forth in Equation 1 is processed via a computer means in a system for continuously measuring hemodynamic state of the patient in terms of mixed venous oxygen saturation. Thus, the computer quantitatively determines and calculates the mixed venous oxygen saturation in the pulmonary artery of the patient as measured transbronchially by the reflectance oximeter fiber-optic probe.

Example 3

Measurements in Human Subjects.

Subject Recruitment and Selection. Subjects are to be selected based on their anticipated surgery and intraoperative monitoring. The bulk of patients are selected from the cardiac surgery schedule, while others will be selected amongst the general surgery population. Only patients receiving a standard single lumen endotracheal tube, and a pulmonary artery catheter, will participate in the study. Thus, it is anticipated that many of these patients are getting elective coronary artery bypass graft procedures and large intra-abdominal procedures (i.e., Whipple's surgery for pancreatic mass).

Data is collected from at least 50 patients over a 6-month period, without inducements to participate in the study. All of the patients undergoing scheduled, elective surgery will have their charts examined the day prior to surgery. When it is anticipated that an embodiment of the present invention is being placed, the attending surgeon will be notified. Prior to proceeding, the purpose and method of the study is explained to the surgeon and the attending anesthesiologist. After a detailed and complete description of the study is presented to the patient and/or caretaker on the day prior to surgery, consent will be obtained using a standard consent form.

Figure 3:
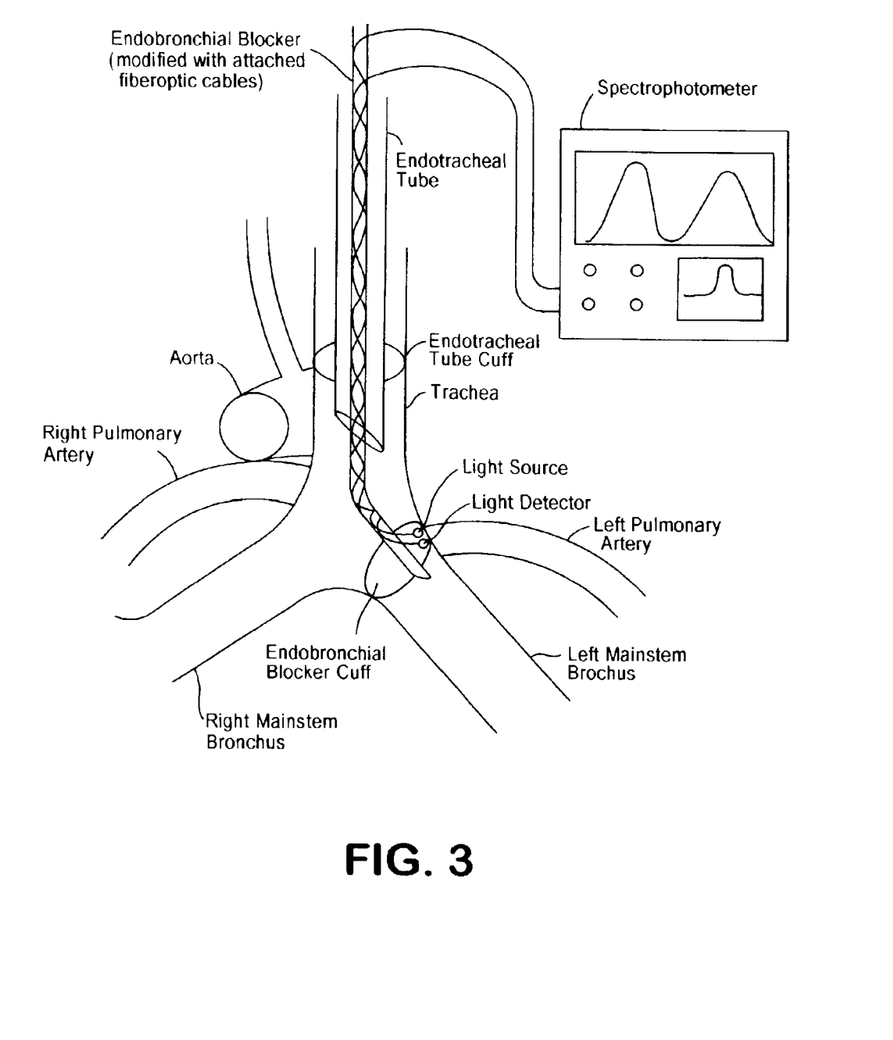
FIG. 3 illustrates a preferred embodiment, wherein the endobronchial blocker modified with attached fiber optic cables has been placed within the left mainstem bronchus of a patient, directly adjacent to the patient's pulmonary artery. The endotracheal tube and the patient's surrounding anatomical features are also shown.

Methods. A standard single lumen endotracheal tube is inserted as shown in FIG. 3. An Arndt endo-bronchial blocker is modified as follows: a fiber optic cable will carry three wavelengths of light (760 nm, 805 nm, 850 nm) from an external source to a point on the outside of the endotracheal tube cuff (FIG. 3). Light is detected at a point also on the outside of the cuff and carried via a fiber optic cable to an external detector. The patient is ventilated with 100% oxygen for at least 5 minutes, at which point ventilation will then be held for 30 seconds. In other embodiments of the invention, alternative fiber-optic devices may be modified in accordance with methods known to one skilled in the art in keeping with descriptions set forth herein.

If the patient's $SpO_2$ (arterial saturation as measured by pulse oximetry) drops to a level greater than 5% from the value on 100% oxygen, the patient will be removed from the study. If the saturation does not fall, the patient is ventilated with 100% oxygen for an additional two minutes, and the study will continue. This test (using 5 minutes of 100% oxygen) occurs only prior to the first measurement, and is meant to ensure that the patient has sufficient pulmonary reserve to tolerate conditions above and beyond that experienced during the procedure. Once the patient is deemed eligible, the blocker is then situated using fiber optic bronchoscopic visualization to a position approximately 1 centimeter proximal to the carina. In the alternative, equivalent reasonable positioning may be selected by practitioners skilled in the art (varying by as much as 10% or 20% or 30% from the preferred proximity to the carina, so long as it is placed in contact with the mucosa of the right bronchus, left bronchus or distal trachea). Measurements are obtained as described in the Data Collection section. The device is then removed when the procedure has been completed, following which the patient is ventilated with 100% oxygen for two additional minutes.

For test purposes, the blocker is subsequently positioned in the proximal left mainstem bronchus and the same information is obtained. Again, the device is removed and the patient is ventilated with 100% oxygen for two additional minutes. Finally, the same procedure is performed in the right mainstem bronchus. The measurements are made once each hour. All placements and adjustments of the device are made only by qualified practitioners.

All of the foregoing ventilation times are intended to be exemplary, and equivalent reasonable alternative times (varying by as much as 10% or 20%) may be selected by practitioners skilled in the art.

Safety Issues/Patient Risk. All of the patients considered for this procedure are those that would be intubated regardless of this procedure. The safety with regards to radiation emitted from the light source on human tissue, in vivo, is well established (Takatani et al., *IEEE Eng. Med. Biol. Mag.* 3:347 (1994); Margreiter et al., *Anesth Analg.* 94:794 (2002); Zonios et al., *Applied Optics* 38(31):6628 (1999); Hull et al., In *Optical Tomography and Spectroscopy of Tissue: Theory, Instrumentation, Model and Human Studies II*, (Chance and Alfano, eds.), SPIE Proc. 2979:355 (1997); Brimacombe et al., *Anesth Analg.* 91:1003 (2000)). Current ANSI guidelines restrict the power of light used on human tissue to 290 $mW/cm^2$. The present device, however, generates only about 0.1 $mW/cm^2$ of light, or less. Since such a low power is delivered, the temperature of the probe does not rise higher than 1° Celcius above ambient temperature.

All bronchial blockers used are either new (i.e., sterilized at the factory and sealed) or reusable. If a reusable tube is used, standard disinfectant and sterilization procedures for in vivo devices will be upheld according to operating room policy. All fiber optic probes are disinfected in a similar manner prior to use on a patient in accordance with hospital or practice guidelines. Thus the main risk to the patient that would not be considered if not part of this study group is hypoxemia (low blood oxygen content), which could occur if there is an inequality of ventilation and perfusion to healthy lungs. Most patients can tolerate one lung ventilation (OLV) without any difficulty. Additionally, given 100% oxygen for approximately 5 minutes in advance of the procedure, most patients can tolerate no ventilation for at least two (2) minutes before blood oxygen saturation levels begin to fall. Thus, the greatest risk to the patient in this study occurs when measurements are made in the distal trachea, when there is no ventilation.

To minimize risk, however many of the following exclusion criteria have been included to assure patients have sufficient pulmonary reserve:

ASA Physical Status>3,

Age>75, Age<18,

Peak inspiratory pressures>35 cm $H_2O$ with double lung ventilation (DLV), $SPO_2$<97% on room air, Current smoker, Morbid obesity (defined as twice ideal body weight), Emergent surgeries, Pregnancy, Previous pneumonectomy and/or bronchial resections, Anticipated double lumen tube placement, Anticipated Monitored Anesthesia Care (MAC)

Any contraindication to pulmonary artery catheter placement,

Neurologic surgery,

Otorhinolaryngologic surgery,

Patient refusal or inability to consent, and

Patients premedicated with ANY sedative prior to consent

Additionally, if at any time during the study desaturation occurs (defined as a drop in $SPO_2$ greater than 5% from point at which patient was breathing 100% oxygen), as a result of placement of the experimental device, the patient will be removed from the study, the device immediately removed, and the surgery will proceed in normal fashion. Removal of the device takes only about 1 second (deflation of the cuff and withdrawal of the endobronchial blocker). Thus, the risk/benefit ratio for this study is extremely low.

Data Collection. After intubation, spectroscopic data is recorded via computer for post-hoc analysis (see FIG. 3). After placement of the pulmonary artery catheter, 3 cc of blood is drawn from the distal port every thirty minutes and sent for rapid co-oximetry measurements. For test purposes, the bronchial blocker is placed (as noted in the Methods section) through the endotracheal tube every 60 minutes and data recorded throughout the duration of the surgery.

In actual use, as opposed to in the foregoing disclosed study, the fiber-optic probe is inserted through an endotracheal tube of the intubated patient only once, e.g., placed in contact with the mucosa of the right bronchus, left bronchus or distal trachea directly adjacent to the pulmonary artery. It would not be moved from site to site on the hour as described. However, it might be moved during the course of the procedure if the first placement location were to prove ineffective. Such a determination is within the skill of the practitioner. The pulmonary artery catheter would only be used in the study for comparative purposes, and is not used in actual practice of the invention.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

We claim:

1. A reflectance oximeter probe device for continuously measuring hemodynamic state of a patient based upon venous oxygen saturation in a cardiac vessel of the patient as determined transbronchially or transtracheally, said device comprising:
    a fiber-optic cable that provides near-infrared light and means for detecting the light,
    a spectrophotometer, and
    an inflatable cuff adapted to be positioned within the bronchus or trachea, wherein the fiber-optic cable and means for detecting the light are operably connected to the spectrophotometer and are arranged on the inflatable cuff to illuminate blood within the cardiac vessel and detect reflectance therefrom.

2. The device of claim 1, wherein venous oxygen saturation comprises mixed venous oxygen saturation in the patient's pulmonary artery.

3. The device of claim 2, wherein the probe is configured to permit insertion into an intubated patient through the patient's endotracheal tube until the probe is placed in contact with and temporarily affixed to the bronchial luminus mucosa of the patient's right bronchus, left bronchus or distal trachea, at a point at which the bronchus or trachea is directly adjacent to the patient's pulmonary artery.

4. The device of claim 3, further comprising a means for measuring scatter of light reflected by oxygenated hemoglobin to quantitatively determine mixed venous oxygen saturation in the pulmonary artery of the patient.

5. The device of claim 1, wherein the inflatable cuff is an endobronchial blocker cuff.

6. The device of claim 1, wherein the inflatable cuff is an endotracheal tube cuff.

7. The device of claim 1, wherein venous oxygen saturation comprises venous oxygen saturation in the patient's superior vena cava.

8. A system for continuously measuring hemodynamic state of a patient in terms of venous oxygen saturation, the system comprising:
    computer means for quantitatively determining venous oxygen saturation in a cardiac vessel of the patient as measured transbronchially or transtracheally by a fiber-optic, near-infrared reflectance oximetric spectroscopy source detector probe;
    the fiber-optic reflectance oximetric probe in accordance with claim 1 for measuring the scatter of light reflected by oxygenated hemoglobin; and
    an algorithm by which venous oxygen saturation is calculated.

9. The system of claim 8, wherein quantitatively determining venous oxygen saturation comprises measuring mixed venous oxygen saturation in the patient's pulmonary artery.

10. The system of claim 9, wherein the calculation is made when arterial oxygen saturation, oxygen consumption and hemoglobin concentration are held constant.

11. The method of claim 8, wherein quantitatively determining venous oxygen saturation comprises measuring venous oxygen saturation in the patient's superior vena cava.

12. A method for continuously measuring hemodynamic state of a patient in terms of venous oxygen saturation, the method comprising:
    placing a fiber-optic cable within the patient's bronchus or trachea;
    transmitting near-infrared light through the bronchial or tracheal wall to illuminate blood within an adjacent cardiac vessel of the patient;
    detecting light reflected from the illuminated blood; and
    measuring venous oxygen saturation in the adjacent cardiac vessel, as determined transbronchially or transtracheally.

13. The method of claim 12, wherein measuring venous oxygen saturation comprises measuring mixed venous oxygen saturation in the patient's pulmonary artery.

14. The method of claim 12, wherein measuring venous oxygen saturation comprises measuring venous oxygen saturation in the patient's superior vena cava.

15. The method of claim 12, wherein measuring is via a reflectance oximeter probe device comprising:
    a fiber-optic cable that provides near-infrared light and means for detecting the light,
    a spectrophotometer, and
    an inflatable cuff adapted to be positioned within the bronchus or trachea,
    wherein the fiber-optic cable and means for detecting the light are operably connected to the spectrophotometer and are arranged on the inflatable cuff to illuminate blood within the cardiac vessel and detect reflectance therefrom.

16. The method of claim 15, wherein measuring venous oxygen saturation comprises measuring mixed venous oxygen saturation in the patient's pulmonary artery.

17. The method of claim 16 for use in a patient, wherein the patient has been intubated, and wherein the method further comprises:
    inserting the probe through the endotracheal tube, and
    placing and temporarily affixing a probe in contact with the bronchial luminus mucosa of the patient's right bronchus, left bronchus or distal trachea, directly adjacent to the patient's pulmonary artery.

18. The method of claim 17, further comprising:
    measuring the scatter of light reflected by oxygenated hemoglobin, and
    quantitatively determining mixed venous oxygen saturation in the pulmonary artery of the patient.

19. The method of claim 18, wherein the patient is in shock.

20. The method of claim 18, wherein the patient is in need of resuscitation.

21. The method of claim 18, wherein the steps are repeated to create a pattern indicating a change in oxygen consumption in the patient.

22. The method of claim 18, wherein the steps are repeated to create a pattern indicating a change in hemoglobin concentration in the patient.

23. The method of claim 18, wherein the steps are repeated to create a pattern indicating a change in cardiac output in the patient.

24. The method of claim 15, wherein measuring venous oxygen saturation comprises measuring venous oxygen saturation in the patient's superior vena cava.

* * * * *